US008589440B1

(12) United States Patent  (10) Patent No.: US 8,589,440 B1
Chaganti et al.  (45) Date of Patent: Nov. 19, 2013

(54) AUTHENTICATION MECHANISMS TO ENABLE SHARING PERSONAL INFORMATION VIA A NETWORKED COMPUTER SYSTEM

(75) Inventors: Naren Chaganti, McLean, VA (US); Sitapathi Rao Chaganti, McLean, VA (US); Damayanti Chaganti, McLean, VA (US)

(73) Assignee: Pennar Software Corporation, Alexandria, VA (US)

( * ) Notice: Subject to any disclaimer, the term of this patent is extended or adjusted under 35 U.S.C. 154(b) by 156 days.

(21) Appl. No.: 13/090,066

(22) Filed: Apr. 19, 2011

Related U.S. Application Data

(63) Continuation of application No. 10/987,917, filed on Nov. 12, 2004, which is a continuation of application No. 09/478,796, filed on Jan. 7, 2000, now Pat. No. 6,845,448.

(51) Int. Cl.
    *G06F 17/30* (2006.01)
(52) U.S. Cl.
    USPC ........................................................ 707/783
(58) Field of Classification Search
    USPC ................... 707/2, 3, 783; 705/64; 709/204; 713/184; 340/5.74
    See application file for complete search history.

(56) References Cited

U.S. PATENT DOCUMENTS

| | | | |
|---|---|---|---|
| RE31,302 E | 7/1983 | Stambler | 340/825 |
| 4,956,769 A | 9/1990 | Smith | 707/9 |
| 5,144,557 A | 9/1992 | Wang | 707/9 |
| 5,204,897 A | 4/1993 | Wyman | 710/200 |
| 5,241,466 A | 8/1993 | Perry | 705/1 |
| 5,247,672 A | 9/1993 | Mohan | 711/152 |
| 5,267,314 A | 11/1993 | Stambler | 380/24 |
| 5,276,901 A | 1/1994 | Howell | 707/9 |
| 5,355,474 A | 10/1994 | Thuraisingham | 395/600 |
| 5,428,778 A | 6/1995 | Brookes | 395/600 |
| 5,475,839 A | 12/1995 | Watson | 395/650 |
| 5,510,777 A | 4/1996 | Pilc et al. | 340/5 |
| 5,524,073 A | 6/1996 | Stambler | 380/24 |
| 5,546,448 A * | 8/1996 | Caswell et al. | 379/142.05 |
| 5,555,303 A | 9/1996 | Stambler | 380/24 |
| 5,608,874 A | 3/1997 | Ogawa | 709/246 |
| 5,612,682 A * | 3/1997 | DeLuca et al. | 340/5.74 |
| 5,621,727 A | 4/1997 | Vaudreuil | 370/60 |
| 5,644,711 A | 7/1997 | Murphy | 713/201 |
| 5,646,998 A | 7/1997 | Stambler | 380/25 |
| 5,694,590 A | 12/1997 | Thuraisingham | 395/600 |

(Continued)

OTHER PUBLICATIONS http://www.freeservers.com, Apr. 29, 1999, pp. 1-3.

(Continued)

*Primary Examiner* — Etienne LeRoux (57) ABSTRACT

System, method and apparatus having the capability of using various authentication mechanisms to share a first party's (user's) personal information stored in a server computer connected to the Internet with a second party (requester). The authentication mechanisms may include a biometric identifier, a single-use password, an expiration time on a password, or permit a second party (requester) to access authorized portions of a first party's (user's) credit/debit card information or likes or dislikes or personal health information from an online database. Also disclosed is a method of providing access to a first party's information using an authentication code that is valid for a predetermined number of access requests and attempting to access the first party's information beyond the predetermined number raises an alarm.

39 Claims, 4 Drawing Sheets

(56) References Cited

U.S. PATENT DOCUMENTS

| | | | |
|---|---|---|---|
| 5,710,578 A | 1/1998 | Beauregard | 345/429 |
| 5,765,152 A | 6/1998 | Erikson | 1/1 |
| 5,767,853 A | 6/1998 | Yoshida | 345/839 |
| 5,793,302 A | 8/1998 | Stambler | 340/825 |
| 5,832,208 A | 11/1998 | Chen | 726/24 |
| 5,832,508 A | 11/1998 | Sherman et al. | 707/300 |
| 5,848,426 A | 12/1998 | Wang | 715/210 |
| 5,931,901 A | 8/1999 | Wolfe | 709/206 |
| 5,936,541 A | 8/1999 | Stambler | 340/825 |
| 5,974,148 A | 10/1999 | Stambler | 380/25 |
| 6,005,939 A | 12/1999 | Fortenberry | 705/76 |
| 6,042,519 A | 3/2000 | Shea | 482/57 |
| 6,070,185 A * | 5/2000 | Anupam et al. | 709/204 |
| 6,073,106 A | 6/2000 | Rozen | 707/9 |
| 6,076,109 A | 6/2000 | Kikinis | 709/228 |
| 6,092,080 A | 7/2000 | Gustman | 707/103 |
| 6,092,196 A | 7/2000 | Reiche | 726/6 |
| 6,139,495 A * | 10/2000 | De La Huerga | 600/300 |
| 6,148,342 A | 11/2000 | Ho | 709/225 |
| 6,175,831 B1 | 1/2001 | Weinreich | 1/1 |
| 6,181,803 B1 | 1/2001 | Davis | 382/115 |
| 6,205,478 B1 | 3/2001 | Sugano et al. | 709/223 |
| 6,266,649 B1 | 7/2001 | Linden | 705/26 |
| 6,269,369 B1 * | 7/2001 | Robertson | 1/1 |
| 6,275,937 B1 | 8/2001 | Hailperin | 713/188 |
| 6,321,334 B1 | 11/2001 | Jerger | 713/200 |
| 6,367,012 B1 | 4/2002 | Atkinson | 713/176 |
| 6,377,161 B1 | 4/2002 | Gromelski | 340/7 |
| 6,405,195 B1 | 6/2002 | Ahlberg | 709/219 |
| 6,453,305 B1 | 9/2002 | Glassman | 705/59 |
| 6,477,580 B1 | 11/2002 | Bowman-Amuah | 709/231 |
| 6,480,958 B1 * | 11/2002 | Harrington | 713/184 |
| 6,487,552 B1 | 11/2002 | Lei et al. | 707/4 |
| 6,496,849 B1 | 12/2002 | Hanson et al. | 709/200 |
| 6,505,160 B1 | 1/2003 | Levy | 704/270 |
| 6,507,865 B1 | 1/2003 | Hanson | 705/36 |
| 6,615,251 B1 | 9/2003 | Klug | 709/218 |
| 6,662,343 B1 | 12/2003 | Gebauer | 715/517 |
| 6,687,745 B1 | 2/2004 | Franco | 709/219 |
| 6,792,458 B1 | 9/2004 | Muret | 709/224 |
| 6,850,916 B1 * | 2/2005 | Wang | 705/64 |
| 6,882,793 B1 | 4/2005 | Fu | 386/241 |
| 7,058,696 B1 | 6/2006 | Phillips | 709/217 |
| 7,155,737 B1 | 12/2006 | Lim | 726/2 |
| 7,167,904 B1 | 1/2007 | Devarajan | 709/218 |
| 7,243,079 B1 | 7/2007 | Manolis | 705/26.8 |
| 7,246,069 B1 * | 7/2007 | O'Hanlon et al. | 705/3 |
| 7,353,199 B1 | 4/2008 | DiStefano | 705/37 |
| 7,599,854 B1 | 10/2009 | Baum | 705/26.1 |
| 7,630,986 B1 | 12/2009 | Herz | 1/1 |
| 2001/0031066 A1 | 10/2001 | Meyer | 382/100 |
| 2001/0050990 A1 | 12/2001 | Sudia | 380/286 |
| 2002/0059402 A1 | 5/2002 | Belanger | 709/220 |
| 2002/0069272 A1 | 6/2002 | Kim | 709/221 |
| 2003/0069874 A1 | 4/2003 | Herzog | 707/1 |
| 2004/0021686 A1 | 2/2004 | Barberis | 345/738 |

OTHER PUBLICATIONS

Chuck Moozakis "Internet Printing Takes Hold" dated Sep. 29, 1998, online article, Retrieved from the Internet on Aug. 10, 2000, URL:http://www.internetwork.com/news0998/news092998-1.htm.
Rolf Blom, et al., Object Security and Personal Information Management, Apr. 27, 2001.
Kelso, "Final Report on the National Integration Resource Center Task Force—The Lisle Report," Apr. 19, 1999, retrieved on Sep. 14, 2000 from http://www.ojp.usdoj.gov/integratedjustice/hsle-fn.htm.
Kendall, et al., "Privacy Impact Assessment for Justice Information Systems," Working Paper, Draft, Jul. 5, 2000, retrieved on Sep. 14, 2000 from http://www.ojp.usdoj.gov/integratedjustice/piajis.htm, pp. 30-31.
Gardner, "Office of Justice Programs, Integrated Justice Privacy Initiative," Apr. 12, 2000, retrieved on Sep. 14, 2000 from http://www.ojp.usdoj.gov/integratedjustice/bp3.htm.
Cavoukian, et al., "Privacy Design Principles for an Integrated Justice System," Working Paper, Apr. 5, 2000, retrieved on Sep. 14, 2000 from http://www.ojp.usdoj.gov/integratedjustice/pdpapril.htm.
J. Michael Murphy, "Privacy Protection—A New Beginning?" 21st International Conference on Privacy and Personal Data Protection, Sep. 13-14, 1999, retrieved on Sep. 14, 2000 from http://www.pco.org.hk/conproceed.html.
Ann Cavoukian, "Privacy and Biometrics," 21st International Conference on Privacy and Personal Data Protection, Sep. 13-14, 1999, retrieved on Sep. 14, 2000 from http://www.pco.org.hk/conproceed.html.
Lorrie Faith Cranor, "Agents of Choice: Tools That Facilitate Notice and Choice About Web Site Data Practices," 21st International Conference on Privacy and Personal Data Protection, Sep. 13-14, 1999, retrieved on Sep. 14, 2000 from http://www.pco.org.hk/conproceed.html.
Austin Hill, "The Privacy Risks of Public Key Infrastructures, 21st International Conference on Privacy and Personal Data Protection", Sep. 13-14, 1999, retrieved on Sep. 14, 2000 from http://www.pco.org.hk/conproceed.html.
Armgard Von Reden, Data Protection Activities in the Private Sector, 21st International Conference on Privacy and Personal Data Protection, Sep. 13-14, 1999, retrieved on Sep. 14, 2000 from http://www.pco.org.hk/conproceed.html.
Nigel Waters, "Re-Thinking Information Privacy—A Third Way in Data Protection?", 21st International Conference on Privacy and Personal Data Protection, Sep. 13-14, 1999, retrieved on Sep. 14, 2000 from http://www.pco.org.hk/conproceed.html.
Hansjuergen Garstka, "The International Working Group on Data Protection in Telecommunications: Common Positions Adopted on Selected Emerging Global Issues," 21st International Conference on Privacy and Personal Data Protection, Sep. 13-14, 1999, retrieved on Sep. 14, 2000 from http://www.pco.org.hk/conproceed.html.
Deborah Hurley, "A Whole World in One Glance: Privacy as a Key Enabler of Individual Participation in Democratic Governance", 21st International Conference on Privacy and Personal Data Protection, Sep. 13-14, 1999, retrieved on Sep. 14, 2000 from http://www.pco.org.hk/conproceed.html.
Robert Gellman, "Public Registers and Privacy: Conflicts with Other Values and Interests," 21st International Conference on Privacy and Personal Data Protection, Sep. 13-14, 1999, retrieved on Sep. 14, 2000 from http://www.pco.org.hk/conproceed.html.
Blair Stewart, "Five Strategies for Addressing Public Register Privacy Problems," 21st International Conference on Privacy and Personal Data Protection, Sep. 13-14, 1999, retrieved on Sep. 14, 2000 from http://www.pco.org.hk/conproceed.html.
David Banisar, "Privacy and Data Protection Around the World," 21st International Conference on Privacy and Personal Data Protection, Sep. 13-14, 1999, retrieved on Sep. 14, 2000 from http://www.pco.org.hk/conproceed.html.
Alfred Bullesbach, "Data Protection and Privacy at a Global Enterprise," 21st International Conference on Privacy and Personal Data Protection, Sep. 13-14, 1999, retrieved on Sep. 14, 2000 from http://www.pco.org.hk/conproceed.html.
Anne Carblanc, "Activities of the OECD—1997-2000—Global Privacy Protection Builds Trust in Electronic Commerce Global Networks", 21st International Conference on Privacy and Personal Data Protection, Sep. 13-14, 1999, retrieved on Sep. 14, 2000 from http://www.pco.org.hk/conproceed.html.
Philip E. Agre, "Imagining Surveillance: Notes on 1984 and Enemy of the State," 21st International Conference on Privacy and Personal Data Protection, Sep. 13-14, 1999, retrieved on Sep. 14, 2000 from http://www.pco.org.hk/conproceed.html.
Roger Clarke, "Person-Location and Person-Tracking: Technologies, Risks and Policy Implications," 21st International Conference on Privacy and Personal Data Protection, Sep. 13-14, 1999, retrieved on Sep. 14, 2000 from http://www.pco.org.hk/conproceed.html.
Simon Davies, "Big Brother at the Box Office—Electronic Visual Surveillance and the Big Screen," 21st International Conference on Privacy and Personal Data Protection, Sep. 13-14, 1999, retrieved on Sep. 14, 2000 from http://www.pco.org.hk/conproceed.html.
Paul, F. Kendall, "Gathering, Analysis and Sharing of Criminal Justice Information by Justice Agenices: The Need for Principles of (56) References Cited

OTHER PUBLICATIONS

Responsible Use," 21st International Conference on Privacy and Personal Data Protection, Sep. 13-14, 1999, retrieved on Sep. 14, 2000 from http://www.pco.org.hk/conproceed.html.
Souheil El Zein, "Reconciling Data Protection Regulations with the Requirements of Judicial and Police Co-operation," 21st International Conference on Privacy and Personal Data Protection, Sep. 13-14, 1999, retrieved on Sep. 14, 2000 from http://www.pco.org.hk/conproceed.html.
Bart De Schutter, International Police Co-operation and Privacy Protection, 21st International Conference on Privacy and Personal Data Protection, Sep. 13-14, 1999, retrieved on Sep. 14, 2000 from http://www.pco.org.hk/conproceed.html.
David H. Flaherty, "Balancing Open Government and Privacy Protection," 21st International Conference on Privacy and Personal Data Protection, Sep. 13-14, 1999, rerieved on Sep. 14, 2000 from http://www.pco.org.hk/conproceed.html.
Michel Gentot, "Access to Information and Protection of Personal Data," 21st International Conference on Privacy and Personal Data Protection, Sep. 13-14, 1999, retrieved on Sep. 14, 2000 from http://www.pco.org.hk/conproceed.html.
Bruno Baeriswyl and Peter Heinzmann, "Privacy Audits with External Experts—Cooperation or Attack?", 21st International Conference on Privacy and Personal Data Protection, Sep. 13-14, 1999, retrieved on Sep. 14, 2000 from http://www.pco.org.hk/conproceed.html.
Stephen Wolley, "Data Security and Privacy Audits Adding Value to the Organisation," 21st—International Conference on Privacy and Personal Data Protection, Sep. 13-14, 1999, retrieved on Sep. 14, 2000 from http://www.pco.org.hk/conproceed.html.
David Flaherty, "How to Do a Privacy and Freedom of Information Act Site Visit," 21st International Conference on Privacy and Personal Data Protection, Sep. 13-14, 1999, retrieved on Sep. 14, 2000 from http://www.pco.org.hk/conproceed.html.
Jane Elizabeth Kirtley, "Privacy and the News Media—A Question of Trust, or of Control?," 21st International Conference on Privacy and Personal Data Protection, Sep. 13-14, 1999, retrieved on Sep. 14, 2000 from http://www.pco.org.hk/conproceed.html.
Raymond Wacks, "Privacy Reconceived: Personal Information and Free Speech," 21st International Conference on Privacy and Personal Data Protection, Sep. 13-14, 1999, retrieved on Sep. 14, 2000 from http://www.pco.org.hk/conproceed.html.
Pamela W.S. Chan, "Consumer Rights and Electronic Commerce," 21st International Conference on Privacy and Personal Data Protection, Sep. 13-14, 1999, retrieved on Sep. 14, 2000 from http://www.pco.org.hk/conproceed.html.
Alan Westin, "Consumers, E-Commerce, and Privacy: US, UK and Germany," 21st International Conference on Privacy and Personal Data Protection, Sep. 13-14, 1999, retrieved on Sep. 14, 2000 from http://www.pco.org.hk/conproceed.html.
Jon Bing, "Data Protection, Jurisdiction and the Choice of Law," 21st International Conference on Privacy and Personal Data Protection, Sep. 13-14, 1999, retrieved on Sep. 14, 2000 from http://www.pco.org.hk/conproceed.html.
Graham Greenleaf, "'IP, Phone-Home' ECMS, © -tech, and Protecting Privacy Against Surveillance by Digital Works," 21st International Conference on Privacy and Personal Data Protection, Sep. 13-14, 1999, retrieved on Sep. 14, 2000 from http://www.pco.org.hk/conproceed.html.
Privacy Commissioner's Office—What's New, retrieved on Sep. 14, 2000 from http://www.pco.org.hk/old_press.html, pp. 1-3.
Naren Chaganti, "Integrating Electronic Message Handling Systems with Databases: A Security Perspective", Masters Thesis, May 1992, The University of Texas at Arlington, Arlington, TX.
3Com, "ReachOut Remote Control Host User's Guide", Jun. 1996, 3Com, pp. 1-63.
3Com, "ReachOut Remote Control Viewer User's Guide", May 1996, 3Com, pp. 1-57.
"Sixdegrees—About Privacy"—from http://www.sixdegrees.com/about/privacy.html dated Apr. 1998, pp. 1-3.

\* cited by examiner

AUTHENTICATION MECHANISMS TO ENABLE SHARING PERSONAL INFORMATION VIA A NETWORKED COMPUTER SYSTEM

CROSS-REFERENCE TO RELATED APPLICATIONS

This is a Continuation Application of Ser. No. 10/987,917 filed Nov. 12, 2004, which is a Continuation Application of Ser. No. 09/478,796, filed on Jan. 7, 2000 (now U.S. Pat. No. 6,845,448 B1).

Subject matter of this Application is related to Ser. No. 12/799,945 filed May 5, 2010 (now U.S. Pat. No. 8,117,644 B1), which is a Continuation Application of Ser. No. 09/634,725 filed Aug. 5, 2010 (now pending), which is a Continuation-in-Part Application of Ser. No. 09/478,796, filed on Jan. 7, 2000 (now U.S. Pat. No. 6,845,448 B1).

FIELD OF THE INVENTION

This invention is related in general to electronic information repositories, and in particular, to a system and method for gathering, storing and disbursing personal information to authorized entities via a communication network.

BACKGROUND

Entities that do businesses on the Internet frequently request visitors to their sites to fill out forms with demographic and other information. Web sites such as the New York Times web site (www.nytimes.com) that provide free access to news, sites such as the Adobe Corporation web site (www.a dobe.com) that provide free downloadable software, sites that provide free magazine subscriptions, sites that provide free or paid services such as a free e-mail account, free Internet access, and similar others, ask a user to fill out a form that includes a user name, contact information, and the like. In some cases the forms are so lengthy that repeated requests for such information causes an annoyance to a user, who would rather get the information or download the software than take the time to fill out a lengthy form. The providers of these forms, however, would like to have as much information about the user as possible, so that they could obtain a profile of the type of persons that are interested in their products or services. It would be useful to both the user and the provider if the user can store all his information at a single location and authorize the release of such information to any person or entity.

Some other examples of entities that request such personal information include credit verification agencies acting on behalf of lenders, utility companies, landlords and the like; and information gathering entities such as health insurance companies, doctor's/dentist's offices, consumer or product surveys, and magazine subscriptions.

With the ubiquity of the public computer networks, commonly known as the Internet or the web, a new way of disseminating personal information has become possible. The meteoric rise of the Internet has enabled it to become a key application development platform. Notwithstanding the availability of these information networks, there is currently no method whereby a user can enter and store his personal information at a single location and selectively authorize it to be distributed to a number of entities. Therefore, there is a need for such as system and method.

Additionally, there is no method whereby the user can update or make changes to the personal information stored at the single location—whether it is a single server computer or a collection of server computers comprising a distributed system—and cause the changes to be distributed to all persons or entities that need to be notified. Accordingly, there is a need for such a system and method.

Further, there is a need for a system which allows a classification of information according to a security or other hierarchical class structure, and provide the classified information to only those entities that have a need to know or are authorized by a person who owns the information. Moreover, there is a need for blocking unauthorized access to such personal information, while allowing access by authorized persons with ease.

Old methods of collecting and disbursing personal credit information required credit reporting agencies to gather and disburse information about individuals and companies, and to disburse this information to entities that request such information. In general, such disbursement is performed after an individual authorizes the release of such information. While these companies gather credit information from several sources, they often provide incomplete or inaccurate information that is not verified by the user until a later date. Additionally, routine form-filling, designating personal preferences such as the user's likes and dislikes, providing fingerprint, retina scan, DNA sequences and other biometric information for later use, or responding to a survey or a health questionnaire is not performed by these credit reporting agencies. These problems with the existing methods can be alleviated by the presented invention as described in the following.

SUMMARY

The present invention is directed toward a method and system for gathering, storing personal information on a server computer and releasing such information to authorized requesters. Several types of information are stored for release to different entities with appropriate authorization.

In one aspect, the present invention is directed toward a method of for automatically disbursing personal information belonging to a user to a requester that is authorized by the user by transmitting said personal information from a server computer operated by a service provider, said server computer coupled to a database, the method comprising the steps of establishing an account for the user with the server computer; assigning an identifier to the user; entering personal information belonging to the user, said personal information comprising at least one of a plurality of information objects; assigning at least one of a plurality of security levels to each information object; storing in the database the user identifier, the information object and the security level assigned to the information object; receiving a request message from the requester, said request message comprising at least the user identifier; retrieving from the database the information object pertaining to the user identifier; securely transmitting the information object to the requester. In a further aspect, the invention comprises the steps of presenting an authorization by the requester; and verifying the requester's authorization.

Further, any modifications, updates, or changes are automatically notified to any authorized requesters. The requester optionally provides information about to whom and where to notify changes, such as address changes. Such change notification can be made by sending a notification to an electronic mail box. In a preferred embodiment, a frequent unauthorized requester of information can be tagged as "junk" requester, to whom no further information will be released.

BRIEF DESCRIPTION OF THE DRAWINGS

These and other objects, features and advantages of the present invention will be more readily understood in the following detailed description of the preferred embodiments and the appended claims with a reference to the drawings, where like numbers indicate like parts in the several views shown, and in which:

DETAILED DESCRIPTION OF THE PREFERRED EMBODIMENTS

Figure 1:
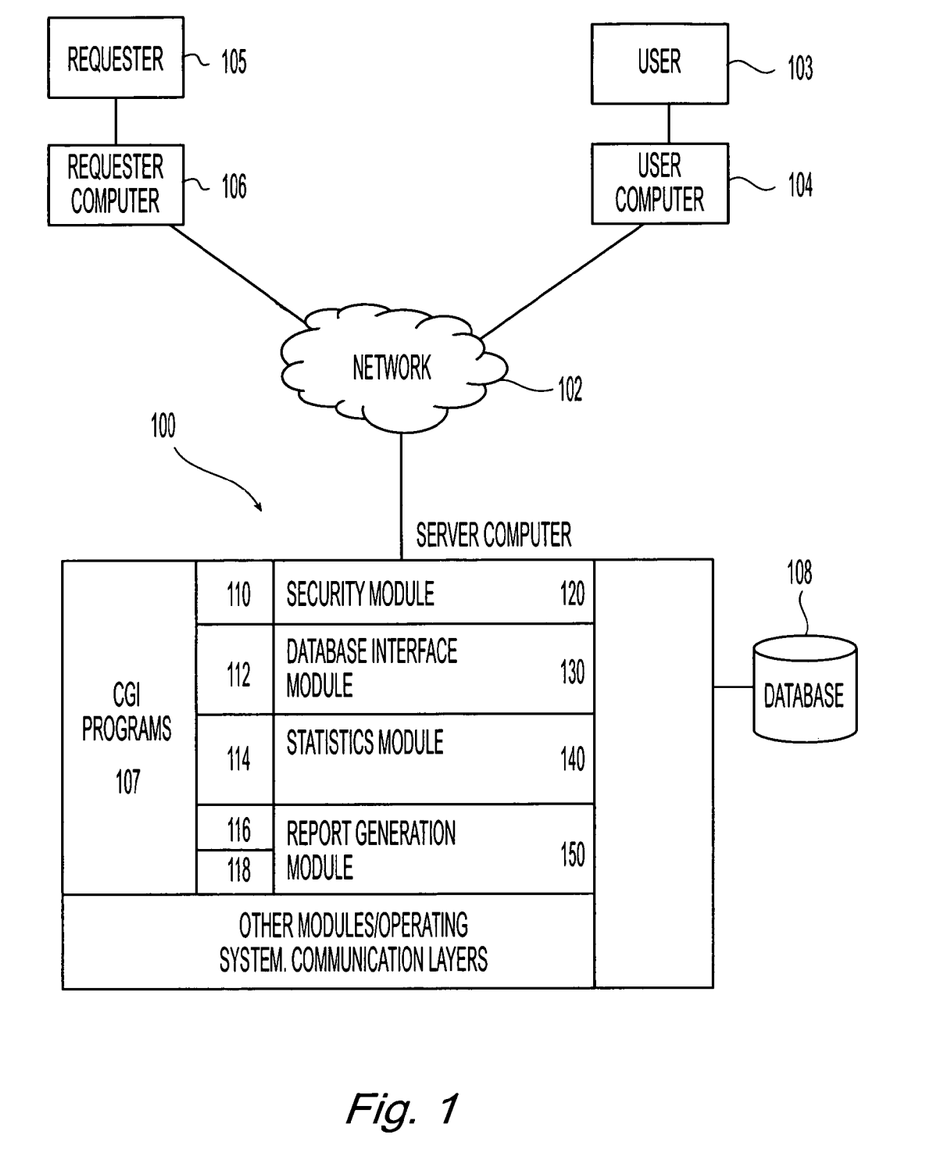
FIG. 1 depicts an architecture comprising a server computer 100, a user computer 104 and a requester computer 106 communicatively coupled to a communication network 102.

Referring to FIG. 1, a server computer 100 configured in accordance with the principles of the present invention is communicatively coupled to a communication network 102 such as the Internet. Also coupled to the communication network 102 is a user 103 operating a user computer 104 and a requester 105 operating a requester computer 106.

The server computer 100 illustratively comprises a microprocessor such as a Compaq® Alpha™ microprocessor, a disk drive, a memory such as a semiconductor memory, and runs an operating system such as Windows-NTT™ or Linux. The server computer 100 is additionally equipped with a data communications device such as a 3-COM™ network card to connect to the network 102. In general, the connection to the network 102 can be established via an Internet Service Provider (ISP) or a direct connection. In a preferred embodiment, the server computer 100 is connected to the network 102 via a high-speed connection such as Digital Subscriber Line.

The server computer 100 is configured to function as a web server. The web server is typically a general purpose computer such as the server computer running software to interface with the Internet using sockets. Commercial suppliers such as Netscape® Corporation of Sunnyvale, Calif. make available such web server software. Additionally, such web server software can also be downloaded and configured free of charge from some sources such as Apache.

Additional programs such as Common Gateway Interface (CGI) programs 107 reside on the server computer. The CGI programs 106 provide for communication and interaction between a user computer 104 and the server computer 100 via the network 102. These CGI programs 107, coupled with data communications software programs, are configured to receive packets of messages from computers connected to the network 102, decipher the information in the packets, and act according to instructions provided in the packets within the constraints imposed by an administrator managing the server computer 100.

In addition to performing the tasks of receiving and sending packets of data from and to the computers connected to the Internet, the CGI programs 107 are configured to perform other tasks such as communicate with a database 108 coupled to the server computer 100, and extract or store information in the database 108 according to the software instructions provided within the server computer 100 or in the packets received from the network 102. Persons skilled in the art can program these CGI programs 107 using programming tools and languages such as C, C++, Java, Perl and Shell scripts.

In an embodiment of the invention, the database 108 comprises a relational database management system, preferably, but not necessarily, with software code to enable Java Database Connectivity. Examples of such products include those marketed by the Oracle Corporation of Sunnyvale, Calif. It should additionally be noted that in an alternative embodiment the database 108 is not needed, or it could comprise software programs executing on the server computer 100.

The server computer 100 is configured to receive request messages from the user computer 104 over the internet in the Hyper Text Transfer Protocol (HTTP), File Transfer Protocol (FTP) or any similar protocol used to transfer data, video, voice or a combination of these media. After analyzing the request messages, the server computer 100 is configured to transmit in response messages that include "web pages" that are programmed in Hyper Text Markup Language (HTML) or a similar language.

Embedded in these web pages are components such as documents, scripts, objects, and frames that are configured to display colorful graphical images on a display device coupled to the user computer 104. Persons skilled in the art know how to make web pages using programming languages or tools such as HTML, Cold Fusion™, Java®, Java Script™, Active Server Pages™ Dynamic HTML, the various markup languages such as Extensible Markup Language (XML), and similar others.

The user computer 104 is equipped with suitable devices and programs to connect to the network 102. In alternative embodiments, the user computer 104 is other device capable of establishing a communication in conjunction with other similar or dissimilar devices over a communication network such as the network 102. Examples of other commercially available digital interactive devices that are contemplated to function in place of the user computer 104 include a telephone, a WebTV™ device marketed by Microsoft Corporation of Redmond, Wash.; a Palm Pilot™ device marketed by 3-COM Corporation of Santa Clara, Calif., or other similar device; the device used in conjunction with the Wireless Web™ service from the Sprint Corporation of Westwood, Kans.; or a Wireless Access Protocol (WAP)-enabled device such as the device marketed by @Motion.com used in conjunction with Wireless Internet service provided by companies such as Phone.com and supported by protocols such as Wireless Markup Language, Mobile Phone Markup Language. Such compatible wireless handset devices are manufactured by Nokia, Motorola, Ericsson, and other companies.

In one embodiment, the user computer 104 is a digital interactive device such as a personal computer comprising a processor similar to a Pentium-III® microprocessor, a display device such as a flat panel display or a CRT, a memory such as semiconductor memory, a storage device such as a disk drive, an input device such as a keyboard, and a pointing device such as a mouse. In other embodiments, there could be provided a microphone or other speech input device and a voice or speech recognizer coupled to the user computer 104, whereupon a user 103 could provide input to the user computer 104 using spoken word commands. Currently, several commercial products are available—either hardware or software or a combination of both—that could be configured to perform speech or voice recognition of spoken words to perform several navigational functions with respect to the web. An example is the product Dragon Dictate™ marketed by Dragon Systems, Inc. of Newton, Mass. In the following, the word "selection" includes clicking a mouse or other pointing device coupled to the user computer 104 at least once; typing at least one character on a keyboard; allowing for a timer to expire; speaking at least one voice command into a microphone coupled to the user computer 104; or touching at least one area on a touch-sensitive screen and other equivalent methods.

In the embodiments described below, a user 103 can navigate the network 102 using either a graphical or a text-based navigational software. Additionally, in a preferred embodiment, the user computer 104 is configured to navigate the network 102 via a browser such as Internet Explorer™ marketed by Microsoft Corporation of Redmond, Wash. Opera™ available at www.opera.com, is a browser configured to enable viewing XML documents. Other browsers such as virtual reality browsers can be used to obtain a three-dimensional experience of the network 102. An example of a text-based browser can be found in the software program Lynx, which is available free of charge.

The requester computer 106 comprises a processor such as a Pentium III microprocessor, a memory such as semiconductor memory, a storage device such as a hard drive, and optionally, a display device such as a CRT or an LCD display, a communications interface device such as a network card to enable connection to the network 102 either directly or via an Internet Service Provider. In alternative embodiments, the requester computer 106 could be a Java Chip enabled terminal device such as a printer directly coupled to the Internet using a protocol such as the Internet Printing Protocol, so that information objects could be directly downloaded and printed on the printer upon transmission by the server computer 100. Preferably, in such cases, there is equipped in the requester computer 106 additional software such as a handshake protocol to ensure a safe delivery of information objects.

In a preferred embodiment, the invention described herein is implemented principally on the server computer 100 and the user 103 interacts with the server computer 100 via a browser program executing on the user computer 104. Similarly, the requester 105 also interacts with the server computer 100 via the requester computer 106.

I. Gathering, Updating and Storing Personal Information

Figure 2A:
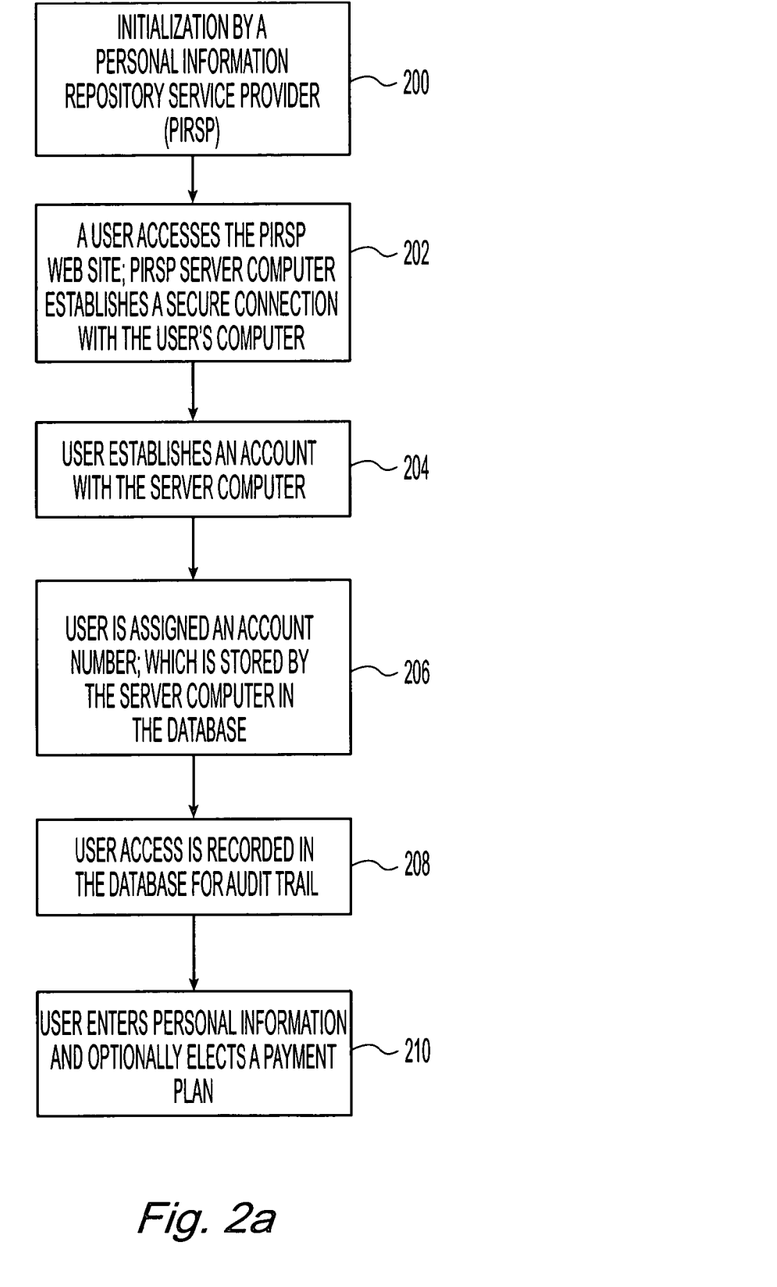
FIG. 2 is a flow chart of steps included in a preferred embodiment.
Figure 2B:
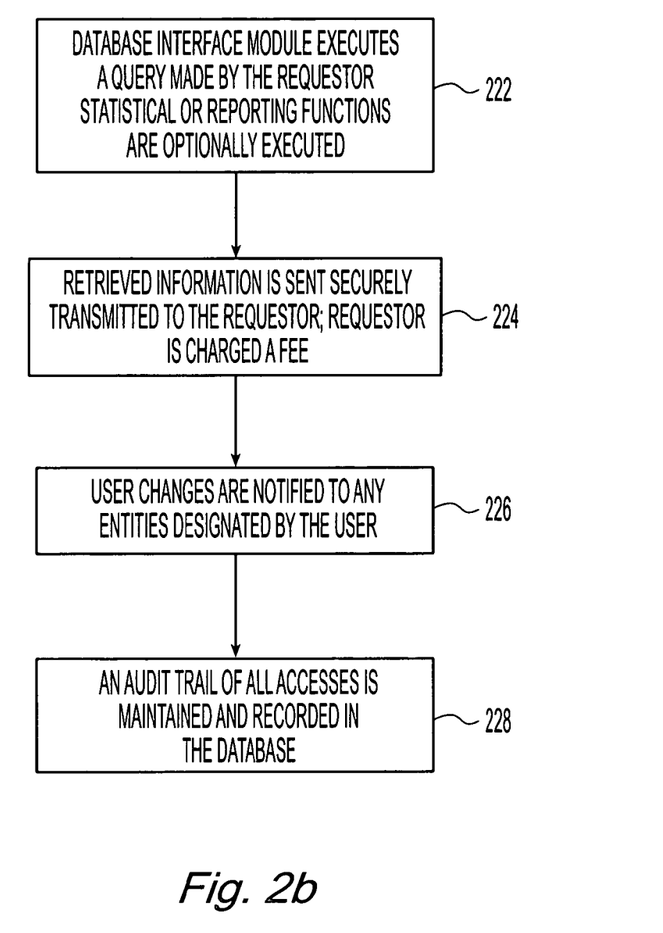

Referring to FIG. 2, the steps included in a preferred embodiment of the invented system are described. During an initialization step (step 200), in a preferred embodiment, a Personal Information Repository Service Provider (PIRSP) operates the server computer 100. In alternative embodiments, there is no service provider such as the PIRSP; and there are other methods of providing such service, such as establishing a personal web site for each user 103, said personal web site comprising information that can be accessed only by an authorized requester 105 in a secure manner; establishing a personal database coupled either directly to the Internet or accessible via the Internet or other communication network; or retrieving information stored elsewhere manually or in an automatic fashion.

Preferably, the PIRSP makes it known to a user 103 that it provides a trusted information repository service. In preferred and alternative embodiments, the PIRSP announces that its services are available free, or for a fee, and in the latter case, the fee is calculated based on a per transaction basis, or on a subscription basis, either from users that store information or from entities that request such information. Other embodiments comprise direct or vicarious payment methods for utilizing the services provided by the PIRSP. These payment methods include an agreement between the PIRSP and the user 103 to generate additional or alternative sources of revenue for the PIRSP via advertisements, referrals, introductions, chain marketing methods and the like.

In this application, any piece of information, however small in granularity or however agglomerated, is referred to as an "information object." Information objects can be implemented in an object-oriented manner, for example, each tuple or a field could be implemented as an object, a data structure or in any other manner known to persons skilled in the art.

Configuring the Database

In a preferred embodiment, the database 108 is a distributed database comprising several components (not shown) such as transaction manager, concurrency controller, memory manager, or a query optimizer. The database 108 is distributed over a large geographical area at several nodes, preferably by partitioning the tables and/or the tuples according to the needs of either the requesters or of the users in each node. The tables or the tuples can be partitioned either vertically or horizontally to enable fast and easy local access. In alternative embodiments, the database 108 is located at a single place.

In the following, a relational database model comprising sets of tuples, meta-data definitions for the tuples, and for other parts of the database organizational schema are described. It should be noted, however, that while a relational database model is described in the preferred embodiment, in alternative embodiments other methods of data definition, which are known to persons skilled in the art, are used. Preferably, the database 108 is configured to comprise a set of relations among several pieces of the user's personal information. These relations are shown in the following as tables according to the following schema. The schema for these tables can be designed by persons skilled in the art.

It should be noted that the user's social security number or alias can illustratively be used as primary keys to access the information from the tables. Other methods, such as date of birth, mother's maiden name, finger print scan, retina scan, or a combination of these methods can be used in other embodiments. The types of fields used in the illustration include Number [0-9]; Character [A-Za-z0-9 and other special characters such as ASCII characters]; and multimedia methods of storage for other types of data.

TABLE 1

Name and Address

| Field Name | Field Type | Field Length |
|---|---|---|
| First Name | Character | 16 |
| Last Name | Character | 16 |
| Middle Name/Initial | Character | 10 |
| Office Address | Character | 22 |
| Work Phone | Number | 10 |
| Mobile Phone | Number | 10 |
| Social Security Number* | Number | 9 |
| Mother's Maiden Name* | Character | 16 |

TABLE 2

Identity and Security

| Identity type | Field Type | Field Length |
|---|---|---|
| Social Security Number* | Number | 9 |
| Mother's Maiden Name* | Character | 16 |
| Password | Character | 16 |
| Password reminder string | Character | 22 |
| E-mail Address | Character | 22 |

The asterisk (*) indicates that the fields could form a primary key to the table. In a preferred embodiment, each field in each tuple is assigned a security classification, the details of which will be discussed below with reference to security.

Referential integrity and Entity integrity of the information objects stored in these tables is preferably ensured. Tables can be joined according to well-known techniques such as inner and outer joins. Views on tables can be formed by combining information objects from several tables. The tables, once formed are preferably normalized to make an efficient usage of the space.

Other tables, the schema for which are not described, are established to store information such as user's contact information (comprising home and work address, telephone and facsimile numbers, address of a nearest relative in case of an emergency, personal web home page address, personal web bookmarks, design of a portal); employment-related information (employer name, address, job title, job classification, salary range, supervisor's name and phone number, and the like); personal demographic information (sex, age, date of birth, marital status, spouse information); property-related information (own/rent home, amount of money in various bank accounts, ownership of stocks or other securities, property ownership information, personal property such as car, boat, private jet, and other details); health related information (types of medication currently used, surgeries undergone, type of drugs that tend to cause allergic reactions, smoking/drinking habits, hospitalization information, status of the several parts of the body, dental records, eye care information, genetic information, family medical history, etc); biometric information (retina scan, samples of speech, finger prints, DNA sequences, and other information); credit related information (rent/mortgage payments, landlord/lender's name, address, phone number, credit card information and the like); personal preferences (movies, travel, books, frequent flier club memberships, important dates such as birthdays, anniversary dates, magazine subscriptions, etc); preferences such as choice of long-distance company, the features used in one's telephone service such as call waiting, call forwarding, three-way calling; names of friends and family members; travel preferences such as preferred airline, class of travel, whether an aisle or a window seat is preferred, whether a rental car is required, what size car is required; hotel preferences such as smoking/non-smoking section, any wake-up call is required, and if so, at what time, the type of amenities preferred or required at the hotel; pleasure-related preferences such as tee-time at a golf course, theater preferences, seat preferences, etc; or preferences for billing and payment methods (cash, credit/debit card, and the like). It should be noted that the type of information that can be stored in these tables can be unlimited. There is no requirement that all the pieces of information need to be furnished, since a requester 105 of information will be provided only that which is made available with the data base 130 or that which is authorized to be released to the requester 105.

A requester 105 that requests information also identifies himself and presents authorization from the user 103. Tables are also devised to store such requester's identification and authorization information for storage in the database 108. All accesses of information are recorded to generate a verifiable audit trail. Tables to store such audit information are designed in the database 108, preferably in a secure partition reachable only by persons with a very high security clearance.

Configuring the Server Computer

In a preferred embodiment, the server computer 100 is configured—in addition to being configured as a web server—to include a number of modules: a user account establishment module 110; a user account management module 112; a personal information collection module 114; a request reception module 116; an authorization verification module 118; a security module 120; a database interface module 130; a statistics module 140; and a report generation module 150. The server computer 100 preferably includes a trusted computer base (TCB) comprising a secure kernel, which includes the security module 120. Most of the security relevant code is stored in the secure kernel. All security relevant events are audited, recorded. Further, events that signal any breach of security are defined and programmed. Upon the occurrence of such an event, an action, including sending an alarm to a predefined entity or person, is performed. Preferably, the modules are implemented as independent memory-resident processes—such as UNIX™ processes—capable of communicating with each other using inter-process communication facilities such as queues, semaphores, sockets, pipes, shared memory and the like. These modules can be programmed by persons skilled in the art using programming languages and techniques such as C, C++, Java or Enterprise Java Beans. It should be noted that the number, nature and functionality of the modules described herein could be differently designed by other designers, and therefore should not be a limiting factor in construing the invention.

Figure 3:
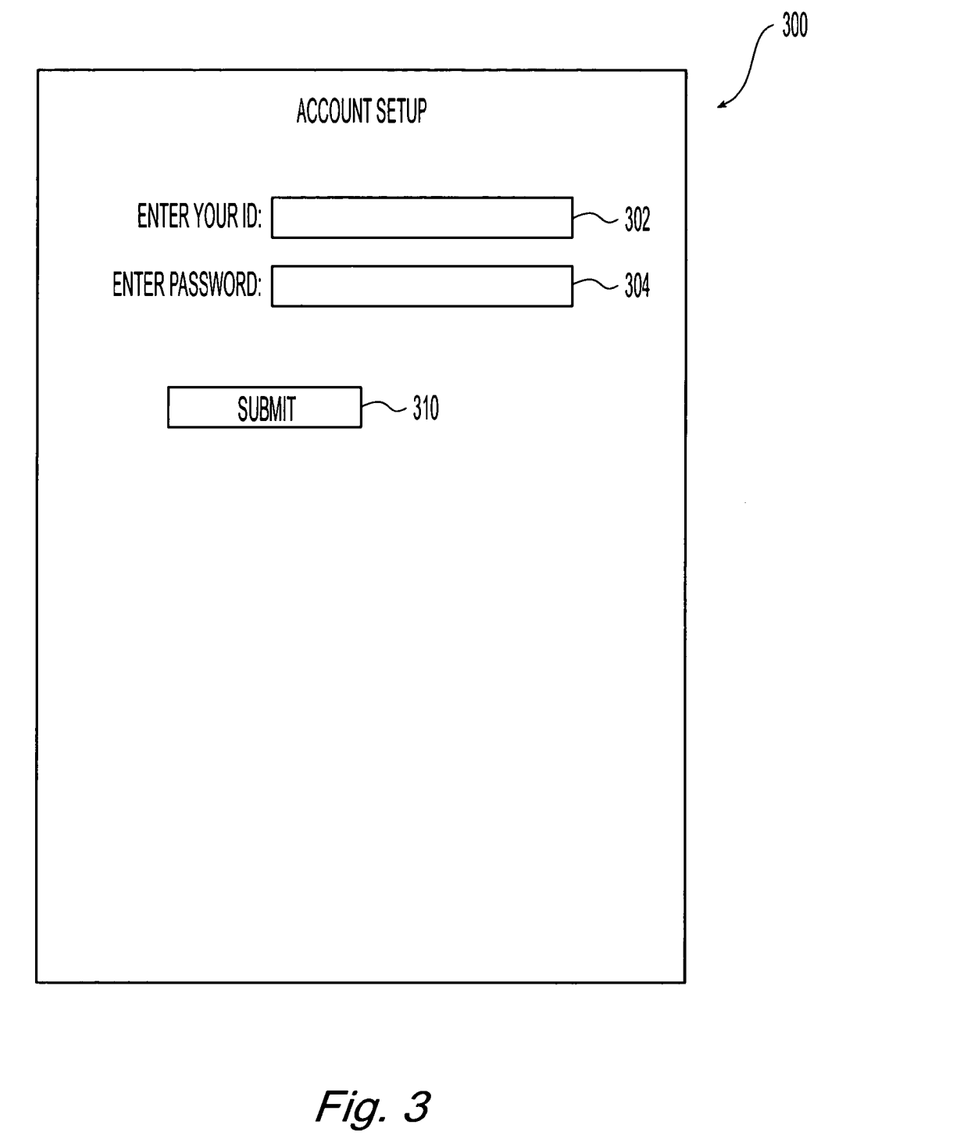
FIG. 3 is an illustrative web page for a user enrollment.

Referring to FIGS. 2 and 3, in a preferred embodiment, the user 103 accesses the PIRSP's web site whereupon the server computer 100 first establishes a secure connection with the user computer 104 (step 202).

The server computer 100 comprises at least one of a plurality of web pages such as the web page 300, which are displayed on the user computer 104. When the web page 300 is displayed, the user 103 is allowed to set up an account with the PIRSP, by entering his name or other identifier in a first text field 302, optionally entering a password string in a second text field 304 and selecting a push button 310 to transmit the web page 300 to the server computer 100 (step 204). In other embodiments, the user 103 provides information to the PIRSP, which information comprises a name, a billing address, a contact E-mail address.

The CGI programs 107 executing on the server computer 100 receive the web page 300, and invoke the user account establishment module 110 to create a new account for the user 103. This process includes allocating an account number to the user 103, which account number is preferably stored in the database 108 (step 206). In a preferred embodiment, this process of receiving and transmitting packets of data is performed by the CGI programs 107 during all interactions with the server computer 100. Therefore, in the following, this description is omitted.

The user account management module 112 comprises code configured to record every access of the user's personal information by the user 103 in the database 108. This establishes an audit trail for a subsequent use (step 208).

The user 103 thereafter enters his personal information such as the kind of information described before, by entering the information via text or other selections made in web pages displayed by the server computer 100 (step 210). It should be noted that since many areas of personal information can be stored by the user 103, it is not required that all such information be entered by the user 103 at one time. For example, the user 103 may initially wish to store his travel preferences and nothing else. This could be because he contemplates travel and wishes to provide this information to his travel agent. Later, the user 103 may enter his medical information and store it in appropriate tables since he wishes to visit his doctor. In this manner, at various times, the user 103 may furnish different aspects of personal information, which will be stored for a future use after it is entered once.

The user account management module additionally allows the user 103 to change or to update the user's password, address, telephone number or any other information. The user can change or update his personal information any time after the account is established. Preferably, the user can also provide a list of entities that should be notified for each change. In one embodiment, each information object that is changed or updated is notified to a list of authorized recipients automatically. In another embodiment, a change or an update is provided to a requester 105 when a request is made.

The user account management module 112 optionally allows the user 103 to select a payment plan for the services rendered by the PIRSP, block any request if the user 103 is in default of a payment, obtain credit card or other verification, and the like. In a preferred embodiment, the payment plans for the user 103 depend on the number of security classifications the user 103 has chosen, the number and nature of the information objects stored by the user 103, the number of requests for information received, the number of accesses or updates made by the user 103 to view and/or change the information objects, the type of customer service requested, the number of entities to which any changes are to be notified, the resources utilized by the user 103, or a combination of these and similar types of activities.

Preferably after user enrollment, the personal information collection module 114 obtains control of the program execution and presents the user 103 with at least one of a series of web pages. These web pages allow the user 103 to provide information to store in corresponding tables described above. In other embodiments, the user provides his information in a paper form, which is entered by the PIRSP into the database 108. Preferably, the user 103 also provides a security classification for each information object, at the tuple or at the field level, by selecting a radio button or a check box for each information object. In a preferred embodiment, there are a predetermined number of security classifications; in other embodiments, there could be a numerical value given to each class of security desired, and the higher the numerical value, the greater is the security classification. No security classification may imply that the information can be released freely to the requester 105, if the user's name is specified.

After the user 103 fills out the web page forms displayed on the client computer 100, the web pages are transmitted to the server computer 100, whereupon the CGI programs 107 receive, parse, and deliver portions of data to the database interface module 130 which stores portions of data entered by the user 103 as information objects in the database 108 in appropriate tables. In a preferred embodiment, the information objects that could be stored in a plurality of tables are collected from the user 103 in a single web page form. In other embodiments, each table or each part of a table can be separately populated with an information object or several objects retrieved from a single web page. In an alternative embodiment, the series of web pages can be displayed as framed or overlapping web pages and the user 103 preferably navigates from one page to another page by simply clicking on a predetermined area on a web page.

Preferably, the user 103 obtains from the server computer 100 at least one key to access his personal information. In one aspect, the key is provided to an authorized entity to enable access of the user's personal information stored in the database 108. There could be a number of types of authorization keys obtainable by the user: a one-time-use-only authorization key, a multiple use authorization key, a qualified authorization key, and others. In another aspect, the attributes encoded in the authorization key allows the release of a specific type of information from the server computer 100. Preferably, these encoded attributes of the authorization key—such as, how many times the authorization can be used to obtain access, what information is accessible using the authorization, any expiration time on the password, whether or not the trustworthiness of the requester is a precondition before releasing the information and the like. In a preferred embodiment, the user 103 specifies these criteria and requests a key from the server computer 100. The key is preferably a string of alphanumeric characters of sufficient length as to prevent being deciphered easily by unscrupulous persons. In other embodiments, the authorization key is preferably encrypted, comprise a spoken word or phrase, a finger print scan, a retina scan, DNA identification, or other forms of identification. These keys could be used in a case such as when the user 103 is unconscious, and an immediate need exists to obtain medical or other information in order to save the patient.

In a preferred embodiment, the database interface module 130 comprises code to establish and verify security classification for each information object stored in the database. Preferably, for each information object, which could be a field, a row, a column, a tuple, or an entire table, a security classification is provided, which is marked on the object. This security classification is preferably an explicit and well-defined policy enforced by the security module 120. Individual accesses of each information object is recorded in the database 108. Each requester is clearly identified and an explicit audit trail for each access is recorded in the database 108. In another aspect, the database interface module 130 operates as a reference monitor as well. The reference monitor mediates all accesses of requests for information objects. Other methods of ensuring security include establishing access control lists for each level of a multi-level security system; a system such as the Signed Document Markup Language (SDML); usage of trusted and known sources such as well-known companies as the requesters, public key encryption, third-party authentication, and other similar techniques.

In a preferred embodiment, potential requesters are also enrolled by the PIRSP in a similar manner as described for the user 103 (step 214). The server computer 100 establishes accounts for potential requesters, allocates identifiers, authenticates their trustworthiness and enables them to establish a payment/billing plan for accessing information objects stored by the user 103. In one embodiment, where there are a number of users, statistical information, rather than individual pieces of information objects are offered for sale to potential requesters. In other embodiments, the potential requesters do not establish accounts with the PIRSP, and will pay as they go for each access of information as described below.

In an embodiment, the user 103 provides his identifier and a secure password, to a requester 105. This could be done, for example, when the user 103 decides to provide a travel agent or a tailor that his personal travel preferences or style and measurements can be obtained from the server computer 100 operated by the PIRSP. In one embodiment, the requester's web page (not shown) comprises an area, selecting which the user 103 can specify that his information can be obtained from the PIRSP's web site. Preferably, the user 103 provides his identifier, a specific authorization—for example to fetch the travel preferences or the medical history and nothing else—and requests the requester 105 to obtain his personal information from the PIRSP. The requester computer 106 is configured to receive this authorization over a secure channel, and to initiate a request to the PIRSP for the user's personal information.

In an alternative embodiment, the requester 105 requests the user 103 manually to fill out a form. This may happen in cases where the user 103 visits a doctor's office, or attempts to establish an appointment with the doctor's office. The doctor's office, which could be enrolled with the PIRSP, may request that the user 103 provide personal information via the PIRSP. The user 103 provides the requester 105 his identifier and authorization to obtain the information from the PIRSP.

II. Securely Disbursing Personal Information

In one embodiment, the PIRSP publicly discloses the database schema, so that any requester 105 can specify the type of information by naming the table and the fields that they want. In other embodiments, the actual database schema are kept secret, but the nature of information that is made available for access by a requester is announced to potential requesters.

The requester 105 preferably establishes a secure connection with the server computer 100 and presents the user's identifier and authorization to the server computer 100 (step 216). Preferably, this process includes the following steps. First, a session with an encrypted Secure Socket Layer connection is established between the requester computer 106 and the server computer 100. Second, the requester 105 transmits at least one packet of data to the server computer 100, said packet of data comprising its identification, its electronic address (either dotted decimal form or other forms), any processor identifier of the requester computer 106. The server computer 100 receives these data and records them in the database 108 along with the time and date when the request is made. Third, the requester computer 106 is configured to present the user's identifier and authorization to the server computer. Alternatively, the requester 105 sends a secure electronic mail (E-mail) to the server computer 100, which E-mail comprises a user identifier, a user-provided authorization key or password, and a request in the form of a database query.

In an alternative embodiment, the requester 105 can be the same as the user 103, such as in case the user 103 wishes to store information for himself, e.g., personal or business phone numbers, E-mail addresses, and other similar information typically stored in a person's wallet, frequent flier numbers, passwords to debit cards, preferences and the like. In this case, an authorization is not required for the user 103 to view information objects stored by him.

Preferably, after authenticating the requester 105, and if the requester 105 is determined to be a genuine entity, a security level is assigned to the requester's request (step 218). The security module 120 verifies the security classification for each field or information object requested before releasing it to the requester 105. Preferably, an information object is released to the requester only if the requester's security classification is at least that of the information object requested. Otherwise, the request is discarded and the attempt by the requester 105 is recorded as a failed request.

In a preferred embodiment, a requester that makes a predetermined number of unauthorized or failed requests is tagged as "junk" requester. The junk requester's identification information is stored in the database 108. A further request from this junk requester is ignored or an alarm message is generated to take an appropriate action (step 220).

The security module 120 preferably performs authentication and verification by assigning a numerical value to the requester 105. Any authorization from the user 103 presented by the requester 105 is also assigned a numerical value. Further, each information object that the requester 105 wishes to access from the server computer 100 is also assigned a numerical value. Preferably, these numerical values represent a corresponding security level for each entity or item to which the value is assigned. In alternative embodiments, numerical values representing security levels are also assigned to the requester's computer 104, the network 102 from which the request arrived at the server computer 100 and other participating entities. The security module 120 thereafter examines the security levels of each entity included in the data transfer process (transaction) to determine the overall security level for the transaction. In a preferred embodiment, any requested information is released to a requester only if the security level of the requester 105 is at least that of all information objects requested. In other embodiments, only those information objects that are at or below the security level of the requester 105 are released to the requester.

In a preferred embodiment, the requester 105 formulates a query, in a readily executable form, preferably in a language such as the Structured Query Language. In other embodiments, the query by the requester 105 is a listing of the information objects requested. The database interface module 130 then executes at least one of a series of queries to extract the information sought by the requester 105 (step 222). The query optimizer included in the database 108 optimally retrieves the stored information after verifying the security level of the request, with the security level designated by the user 103 for an information object.

Several alternative methods of accessing information are used by the security module 120 and the database interface module 130. In one method, the database interface module 130 retrieves an information object if the security level of that information object is at or below the security level for the request and that of the authorization. In another embodiment, a data base view is automatically defined to extract all individually classified information objects, and in this case, if the security level of an information object is above the security level for the request, a blank entry is returned. Alternatively, the database interface module 130 may insert an indication instead of a blank entry, which indication specifies that either the information is not available, or it is available for a requester with a higher security level, and the like.

In another embodiment, the user 103 requests the PIRSP to disburse information to the requester 103 using an electronic means (step 224). In this case, the user is authenticated and the information objects are downloaded or transmitted to the requester 105, preferably via secure E-mail, file transfer protocol, after establishing a circuit-switched connection, facsimile, U.S. mail or any other method.

Preferably, the requester 105 is forbidden from reselling or retransmitting the information, or using it beyond an expiration date set either by the user 103 or by the PIRSP. Preferably, to ensure this, information objects are copyrighted or otherwise contractually protected. Further, this could be a selling point to users, since the PIRSP not only guarantees the safety of the stored information, but in addition controls how this information is used.

In one embodiment, the requester 105 is charged a fee for receiving the information objects, on a per object basis, or on a subscription basis or for receiving statistical reports. The PIRSP may provide an incentive to the user 103 by paying the user 103 a portion of the fee to the user 103. In another embodiment, a requester may receive statistical report such as "how many male golf players between the ages 22 and 55 in the zip code 20006 are interested in trading stocks?" The statistics module 140 and report generation module 150 make appropriate queries in the database 108 and obtain the information. Preferably such statistical information is not considered secure, unless it has a tendency to reveal too much about the private habits of the user 103. Thus, so long as information is aggregated and can remain anonymous, it will be released to potential requesters to assist marketing of products/services.

The user 103 may change or update his personal information. Examples of changes could be address or telephone number changes, and the like. Some changes are effective at a future date. Some information is updated either by the user 103 or by a third party (not shown). An example of such updated information is medical information. When the user 103 makes the changes, he makes these by accessing the server computer 100 web site and entering his information as described above. The user 103 elects or designates any requesters or recipients of change notifications. The server computer 100 automatically retrieves the information objects that changed and notifies the designated requesters or recipients via secure E-mail, or other methods indicated above (step 226). In alternative embodiments, notification messages are left in mail boxes located on the server computer 100 and owned by requesters. Each change notification is recorded in the database 108 for audit trail purposes.

In a preferred embodiment, every time an information object is accessed, an entry is made into the database 108 and a secure audit trail established (step 228). This audit trail is preferably designed to track the activities of the PIRSP as well as the activities of the user 103 and the requester 105. This ensures that a clear audit is preserved to determine and prevent any misuse of personal information. Preferably such audit trail is established by programming in the secure kernel included in the server computer 100. All activities are stored in a specially partitioned area of the database 108 and are read-only after written by any process.

The foregoing describes a method and a system for obtaining, storing and automatically disbursing personal information over a communications network. Though reference is made only to a single instance of each of the client and the server computers, it should be noted that the invention can be practiced using an architecture comprising a plurality of client computers (not shown) and/or a plurality of server computers (not shown). Additionally, though reference is made only to a single processor computer, the server or the client computer could comprise a distributed, parallel computing environment, either including a single-processor or a multiple-processor architecture, whether symmetric or asymmetric. In alternative embodiments, the user 103 operating the user computer 104 is thought to interact with the server computer 100 using a model such as that facilitated by the Java Bean, the Enterprise Java Bean or other similar technologies such as Remote Method Invocation, Distributed Component Object Model. Sessions could be implemented by using stateful or stateless Enterprise Java Beans and the like. The database 108 can be accessed via session or other kinds of beans, either a single instance of them or via numerous instances managed by another object layer. In alternative embodiments, the invention described herein can be implemented in part on the server computer 100 and in part on the user computer 104, in part as a servlet, as a downloaded JavaScript™ program, as a plug-in program, as an applet, or any combinations thereof. In alternative embodiments, the server computer 100 is located behind a fire-wall, and may store a cookie, download a Dynamic HTML script, a JavaScript program or a plug-in program to the user computer 104 to achieve a portion of the functionality described herein. In one embodiment, no software is deposited on the user computer 104 other than the HTML page displayed on a browser. The word "network" comprises any heterogenous or homogenous collection of computer networks, public or private or a combination of both, which network includes intelligent or "passive" elements; either wholly or partly, and further includes routers, bridges and other transport mechanisms; executing a single protocol or a combination of a plurality of data communication protocols; effecting communication (transmission and/or reception) of information, which information comprises voice, video, data, and/or text or any combinations thereof; using either in-band or out-of-band methods. The word "database" is assumed to comprise a flat file, an area in memory, an index file, a relational database, a sequential or a random access data storage and retrieval method operating in conjunction with any type of device, a distributed database or a single database, and could further comprise a relational database, hierarchical, sequential, random access or any other type of database, with or without a transaction manager, concurrency controller, memory manager, or a query optimizer. Further, the steps described herein are illustrative and not limiting, and the order of the steps described could be altered. Moreover, some of the steps could be collapsed into a single step, while some other steps are superfluous or optional and are described only to elaborate the principles of the invention. Persons skilled in the art may make modifications, rearrangements and adjustments to the disclosed preferred embodiments without undue experimentation or without significantly departing from the spirit and scope of the appended claims, which claims should be construed to include all these modifications, rearrangements, adjustments, and departures.

What is claimed is:

1. A method of sharing a first party's information with a second party based on multi-factor authentication, the method comprising the following steps performed by a server computer:
    establishing an account for a first party;
    storing one or more information objects in the first party's account;
    receiving a first request to access one or more information objects stored in the first party's account from a second party, the first request accompanying a first authentication mechanism and a second authentication mechanism; and
    enabling access by the second party to the one or more information objects stored in the first party's account if the first request is authenticated under the first authentication mechanism and the second authentication mechanism, whereby the second party accesses the one or more information objects authorized by the first party.

2. The method of claim 1, wherein the first authentication mechanism or the second authentication mechanism includes an authorization key that can be used a pre-determined number of times.

3. The method of claim 1, wherein the first authentication mechanism or the second authentication mechanism includes a one-time-use authorization key.

4. The method of claim 1, wherein the first authentication mechanism or the second authentication mechanism includes an authorization key that expires after a predetermined time.

5. The method of claim 1, wherein the first authentication mechanism or the second authentication mechanism includes trustworthiness of a requester.

6. The method of claim 1, wherein the first authentication mechanism or the second authentication mechanism includes a biometric authorization key.

7. The method of claim 1, wherein first authentication mechanism or the second authentication mechanism includes (a) retina scan, (b) speech sample, (c) finger print, or (d) DNA information.

8. The method of claim 1, wherein the first authentication mechanism or the second authentication mechanism includes a first code enabling access to specified category of information objects.

9. The method of claim 8, wherein the first code enables the requester to obtain only the first party's credit card or debit card information.

10. The method of claim 8, wherein the first code enables the requester to obtain only the first party's financial information.

11. The method of claim 8, wherein the first code enables the requester to obtain only the first party's personal likes and dislikes.

12. The method of claim 8, wherein the first code enables the requester to obtain only the first party's health information.

13. The method of claim 8, wherein the first code enables the requester to obtain only the first party's employment information.

14. The method of claim 8, wherein the first code enables the requester to obtain only the first party's travel preferences.

15. A server computer system configured to share a first party's personal information with a second party comprising:
a processor,
a memory, the memory coupled to the processor,
wherein the memory is configured to provide the processor with instructions which when executed cause the processor to:
establish an account for a first party;
store one or more information objects in the first party's account;
receive from a second party a first request to access one or more information objects stored in the first party's account, said first request accompanying a first authentication mechanism and a second authentication mechanism; and
enable access to the one or more information objects stored in the first party's account if the first request is authenticated under the first authentication mechanism and the second authentication mechanism, whereby the second party accesses the one or more information objects authorized by the first party.

16. A method of using a an N-time (N, where N≥1) authorization key to access a first party's information stored in the first party's account established on a server computer, said method comprising the following steps performed on the server computer:
receiving a request from a requester to access a first portion of the first party's information, said request including:
the requester's identification information,
the first party's identification information;
an authentication code, said authentication code being configured to be used a predetermined number (N, where N≥1) of times to access the first portion of the first party's information; and
enabling the requester to access the first portion of the first party's information if the number (n) of times the request is made using the authorization code does not exceed N.

17. The method of claim 16, further comprising the step of:
generating an alarm condition if the number (n) of times a request is made by the requester for the first party's information exceeds N.

18. The method of claim 16, wherein the first portion of the party's information is the first party's credit card information, debit card information, personal health record, medical information, employment information, or personal preferences.

19. The method of claim 16, further comprising the steps of:
associating each of a plurality of portions of information in the first party's account with an identifier, each said identifier being used to enable selection of a specific portion of the first party's information.

20. The method of claim 16,
wherein the authentication code includes biometric information, an indication of trustworthiness of the requester, an address from which a request is received, a processor identifier of the requester computer, or time and/or date of the request.

21. A non-transitory computer-readable storage medium storing program code for causing a server computer to perform a method of sharing a first party's information with a second party based on multi-factor authentication, the method comprising the following steps performed on the server computer:
establishing an account for a first party;
storing one or more information objects in the first party's account;
receiving a first request to access one or more information objects stored in the first party's account from a second party, the first request accompanying a first authentication mechanism and a second authentication mechanism; and
enabling access by the second party to the one or more information objects stored in the first party's account if the first request is authenticated under the first authentication mechanism and the second authentication mechanism, whereby the second party accesses the one or more information objects authorized by the first party.

22. The non-transitory computer-readable storage medium storing program code as in claim 21, wherein the first authentication mechanism or the second authentication mechanism includes an authorization key that can be used a pre-determined number of times.

23. The non-transitory computer-readable storage medium storing program code as in claim 21, wherein the first authentication mechanism or the second authentication mechanism includes a one-time-use authorization key.

24. The non-transitory computer-readable storage medium storing program code as in claim 21, wherein the first authentication mechanism or the second authentication mechanism includes an authorization key that expires after a predetermined time.

25. The non-transitory computer-readable storage medium storing program code as in claim 21, wherein the first authentication mechanism or the second authentication mechanism includes trustworthiness of a requester.

26. The non-transitory computer-readable storage medium storing program code as in claim 21, wherein the first authentication mechanism or the second authentication mechanism includes a biometric authorization key.

27. The non-transitory computer-readable storage medium storing program code as in claim 21, wherein first authentication mechanism or the second authentication mechanism includes (a) retina scan, (b) speech sample, (c) finger print, or (d) DNA information.

28. The non-transitory computer-readable storage medium storing program code as in claim 21, wherein the first authentication mechanism or the second authentication mechanism includes a first code enabling access to specified category of information objects.

29. The non-transitory computer-readable storage medium storing program code as in claim 28, wherein the first code enables the requester to obtain only the first party's credit card or debit card information.

30. The non-transitory computer-readable storage medium storing program code as in claim 28, wherein the first code enables the requester to obtain only the first party's financial information.

31. The non-transitory computer-readable storage medium storing program code as in claim 29, wherein the first code enables the requester to obtain only the first party's personal likes and dislikes.

32. The non-transitory computer-readable storage medium storing program code as in claim 28, wherein the first code enables the requester to obtain only the first party's health information.

33. The non-transitory computer-readable storage medium storing program code as in claim 28, wherein the first code enables the requester to obtain only the first party's employment information.

34. The non-transitory computer-readable storage medium storing program code as in claim 28, wherein the first code enables the requester to obtain only the first party's travel preferences.

35. A non-transitory computer-readable storage medium storing program code for causing a server computer to perform a method of an N-time (N, where N≥1) authorization key to access a first party's information stored in the first party's account established on a server computer, said method comprising the following steps performed on the server computer:
   receiving a request from a requester to access a first portion of the first party's information, said request including:
   the requester's identification information,
   the first party's identification information;
   an authentication code, said authentication code being configured to be used a predetermined number (N, where N≥1) of times to access the first portion of the first party's information; and
   enabling the requester to access the first portion of the first party's information if the number (n) of times the request is made using the authorization code does not exceed N.

36. The non-transitory computer-readable storage medium storing program code as in claim 35, the program code further configured to perform the step of:
   generating an alarm condition if the number (n) of times a request is made by the requester for the first party's information exceeds N.

37. The non-transitory computer-readable storage medium storing program code as in claim 35,
   wherein the first portion of the party's information is the first party's credit card information, debit card information, personal health record, medical information, employment information, or personal preferences.

38. The non-transitory computer-readable storage medium storing program code as in claim 35, the program code further configured to perform the step of:
   associating each of a plurality of portions of information in the first party's account with an identifier, each said identifier being used to enable selection of a specific portion of the first party's information.

39. The non-transitory computer-readable storage medium storing program code as in claim 35, wherein the authentication code includes biometric information, an indication of trustworthiness of the requester, an address from which a request is received, a processor identifier of the requester computer, or time and/or date of the request.

\* \* \* \* \*

UNITED STATES PATENT AND TRADEMARK OFFICE
CERTIFICATE OF CORRECTION

PATENT NO.        : 8,589,440 B1
APPLICATION NO.   : 13/090066
DATED             : November 19, 2013
INVENTOR(S)       : Naren Chaganti, Sitapathi Rao Chaganti and Damayanti Chaganti It is certified that error appears in the above-identified patent and that said Letters Patent is hereby corrected as shown below:

In the Specification

Col. 1, line 16, please change "August 5, 2010" to --August 5, 2000--.

In the Claims

Col. 15, lines 22-63, replace Claims 16-17 with the following:

16. A method of using an N-time authentication code to provide access to a first party's information stored in the first party's account established on a server computer, said method comprising the following steps performed on the server computer:
receiving a request from a requester to access a first portion of the first party's information, said request including
the requester's identification information,
the first party's identification information;
an authentication code, said authentication code being configured to be used a predetermined number (N, where $N \geq 1$) of times to access the first portion of the first party's information; and
enabling the requester to access the first portion of the first party's information if the number (n) of times the request is made using the authentication code does not exceed N.

17. The method of claim 16, further comprising the step of:
generating an alarm condition if the number (n) of times a request is made using the authentication code for the first party's information exceeds N.

Signed and Sealed this
Thirty-first Day of December, 2013

Margaret A. Focarino
*Commissioner for Patents of the United States Patent and Trademark Office*

Col. 17, lines 25-31 and Col. 18, lines 1-15, replace Claims 35-36 with the following:

35. A non-transitory computer-readable storage medium storing program code for causing a server computer to perform a method of using an N-time authentication code to provide access to a first party's information stored in the first party's account established on a server computer, said method comprising the following steps performed on the server computer:
  receiving a request from a requester to access a first portion of the first party's information, said request including
    the requester's identification information,
    the first party's identification information;
    an authentication code, said authentication code being configured to be used a predetermined number (N, where $N \geq 1$) of times to access the first portion of the first party's information; and
  enabling the requester to access the first portion of the first party's information if the number (n) of times the request is made using the authentication code does not exceed N.

36. The non-transitory computer-readable storage medium storing program code as in claim 35, the program code further configured to perform the step of:
  generating an alarm condition if the number (n) of times a request is made using the authentication code for the first party's information exceeds N.